(12) United States Patent
Nolan et al.

(10) Patent No.: US 9,808,404 B2
(45) Date of Patent: Nov. 7, 2017

(54) PROVIDING A REMINDER TO A USER THAT HAS AN IMPACT ON THE USER

(71) Applicant: KONINKLIJKE PHILIPS N.V., Eindhoven (NL)

(72) Inventors: Julian Charles Nolan, Pully (CH); Melanie Jane Windridge, Amersham (GB); Alex Marshal, Lausanne (CH); Joyca Petra Wilma Lacroix, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/105,021

(22) PCT Filed: Dec. 8, 2014

(86) PCT No.: PCT/EP2014/076804
§ 371 (c)(1),
(2) Date: Jun. 16, 2016

(87) PCT Pub. No.: WO2015/091040
PCT Pub. Date: Jun. 25, 2015

(65) Prior Publication Data
US 2016/0354285 A1 Dec. 8, 2016

(30) Foreign Application Priority Data
Dec. 17, 2013 (EP) ..................... 13197710

(51) Int. Cl.
*G08B 21/00* (2006.01)
*A61J 7/04* (2006.01)
(Continued)

(52) U.S. Cl.
CPC ........ *A61J 7/0481* (2013.01); *G06F 19/3462* (2013.01); *G06Q 10/109* (2013.01);
(Continued)

(58) Field of Classification Search
CPC .. A61J 7/0481; G06F 19/3462; G06Q 10/109; G08B 21/24
(Continued)

(56) References Cited

U.S. PATENT DOCUMENTS 7,304,582 B2   12/2007   Kerr, II et al.
7,317,803 B1   1/2008    Prabhakar et al.
(Continued)

FOREIGN PATENT DOCUMENTS

EP   1852789 A1   11/2007
EP   2485704 A1   8/2012
(Continued)

OTHER PUBLICATIONS

Castignani et al, "A Study of the Discovery Process in 802.11 Networks", ACM Sigmobile Mobile Compouting and Communications Review, vol. 15, No. 1, 2011, pp. 25-36.
(Continued)

*Primary Examiner* — Mark Rushing (57) ABSTRACT

A system for providing a reminder to a user is provided that comprises a reminder datastore arranged to store reminder information relating to a task for the user to be reminded about, and a reminder processor arranged to determine a time at which the reminder is due, based on the reminder information. A locating mechanism is provided to obtain information relating to a location of the user, and an output mechanism is provided to output reminder alerts through one or more reminder devices. The reminder processor is arranged to obtain information relating to a location of the user for the time at which the reminder is due, from the locating mechanism, and to identify one of the one or more reminder devices in proximity to said location of the user, based on known locations of the one or more reminder
(Continued)

devices. The output mechanism is arranged to output a reminder alert through the identified reminder device.

14 Claims, 6 Drawing Sheets

(51) Int. Cl.
  *G06F 19/00*    (2011.01)
  *G06Q 10/10*    (2012.01)
  *G08B 21/24*    (2006.01)

(52) U.S. Cl.
  CPC ........... *G08B 21/24* (2013.01); *A61J 2200/30* (2013.01); *A61J 2205/70* (2013.01)

(58) Field of Classification Search
  USPC .................................................... 340/539.12
  See application file for complete search history.

(56) References Cited

U.S. PATENT DOCUMENTS

| | | | |
|---|---|---|---|
| 2002/0093429 A1* | 7/2002 | Matsushita | A61J 7/0481 340/573.1 |
| 2006/0154642 A1 | 7/2006 | Scannell | |
| 2008/0195312 A1* | 8/2008 | Aaron | G06Q 10/109 455/418 |
| 2009/0106382 A1 | 4/2009 | Arellano et al. | |
| 2010/0073169 A1 | 3/2010 | Needham et al. | |
| 2011/0022224 A1 | 1/2011 | Park | |
| 2011/0029647 A1 | 2/2011 | Ginevan et al. | |
| 2012/0313785 A1 | 12/2012 | Hanson et al. | |
| 2013/0179472 A1 | 7/2013 | Junqua et al. | |
| 2013/0222135 A1 | 8/2013 | Stein et al. | |

FOREIGN PATENT DOCUMENTS

| | | |
|---|---|---|
| WO | 2006023097 A1 | 3/2006 |
| WO | 2011042840 A1 | 4/2011 |

OTHER PUBLICATIONS

12 Alarm Cadex Silver Medication Reminder and Alert Watch, Downloaded Form http://www.cadexwatch.com/952431-cadex-sliver-12-alarm-medication-reminder-amp-ale.html, on Jun. 13, 2016, 3 Pages.

Cadex E-Pill Devices, Downloaded Form http://www.cadexwatch.com/order.html, on Jun. 13, 2016, 8 Pages.

4 Alarm Pill Box Organizer With Vibration Reminder, Downloaded From http://www.cadexwatch.com/pocketalarm.html on Jun. 13, 2016, 2 Pages.

How the MEM-X Voice Reminder Works, Downloaded From Http://www.pivotell.co.uk/how-the-mem-x-voice-reminder-works.htm.

Pivotell Advance Dispenser, Dowloaded From http://www.pivotell.co.uk/pivotell+advance+dispenser/0_caaa001/praa001.htm on Jun. 13, 2016.

Philips Medication Dispensing Service, Downloaded From http://www.caregiverreviews.com/philips-mediciation-dispensing-service-technology on Jun. 13, 2016, 5 Pages.

\* cited by examiner

PROVIDING A REMINDER TO A USER THAT HAS AN IMPACT ON THE USER

CROSS-REFERENCE TO PRIOR APPLICATIONS

This application is the U.S. National Phase application under 35 U.S.C. §371 of International Application No. PCT/EP2014/076804, filed on Dec. 8, 2014, which claims the benefit of European Patent Application No. 13197710.0, filed on Dec. 17, 2013. These applications are hereby incorporated by reference herein.

FIELD OF THE INVENTION

The present invention relates to a system and method for providing a reminder to a user.

BACKGROUND OF THE INVENTION

There are many reasons why users may wish to be reminded about activities. Ways of alerting reminding users of activities have existed for a long time. These range from old-fashioned alarms to web-based or mobile device applications. Taking a mobile device application as an example, a user will typically set a task (e.g. buy more milk) and a time to be reminded (e.g. tomorrow at 8:00 am). The mobile device application will then issue the reminder (e.g. using an audible alert with an onscreen notification) at the preset/predefined time.

There are many situations where the reminder is very important. For example, a patient with a long term health condition may have a therapeutic regime prescribed by a doctor, that the patient should then adhere to at set time periods or within certain time boundaries. The therapeutic regime may manage the patient's symptoms, with the objective of the therapeutic regime being to manage the patient's condition and to help to achieve a positive therapy outcome. It will be appreciated that non-adherence with the therapeutic regime may cause the patient's health to deteriorate.

For many long term health conditions, the therapeutic regime requires medication to be taken regularly (e.g. one dose, three times a day). If the medication is not taken regularly, or is not taken in the correct amounts (i.e. if the therapeutic regime is not adhered to), the clinical outcome may be impacted. It is known to use conventional reminder system approaches (e.g. mobile device applications) to attempt to encourage users to adhere to their therapeutic regime (e.g. by taking their medication on time).

It is also known to provide dedicated devices for medication management. These are generally dispensers that can be programmed to issue alerts and release medication at pre-defined times. They often include a means of monitoring compliance by way of detecting if the medication has been removed from the dispenser. As an example of such devices, EP2485704 discloses a medication dispenser that provides a reminder in the form of light and sound emitted by the dispenser itself The dispenser can connect to a remote server to exchange information on the dispensing and the patient's adherence.

All the conventional systems mentioned above provide reminders through a preset device at preset times of the day, depending on how they are configured. This approach is, however, inflexible. As a consequence, it allows for providing reminders at moments when the user is not in the vicinity of the device, in which case the user will miss the reminder.

SUMMARY OF THE INVENTION

It is an object of the invention to provide a system for providing a reminder to a user which substantially alleviates or overcomes the problems mentioned above. In particular, it is an object of the invention to provide a system for providing a reminder to a user that overcomes the technical shortcomings of known messaging systems.

According to the present invention, there is provided a system for providing a reminder to a user, the system comprising: a reminder datastore arranged to store reminder information relating to a task for the user to be reminded about; a reminder processor arranged to determine a time at which the reminder is due, based on the reminder information; a locating mechanism arranged to obtain information relating to a location of the user; and an output mechanism arranged to output reminder alerts through one or more reminder devices, wherein the reminder processor is arranged to obtain information relating to a location of the user for the time at which the reminder is due, from the locating mechanism, and to identify one of the one or more reminder devices in proximity to said location of the user, based on known locations of the one or more reminder devices, and wherein the output mechanism is arranged to output a reminder alert through the identified reminder device.

This arrangement provides the advantage that reminders are provided through a device that is currently nearby to the user, maximizing the chance that the reminder will be recognized by the user.

In some embodiments, the system further comprises a ranking processor arranged to assign a ranking score to each of the reminder devices, with the ranking score relating to the likely impact of a reminder alert provided through a said reminder device, wherein the reminder processor is arranged to identify the reminder device by selecting one of a plurality of the reminder devices in proximity to said location of the user, in consideration of the ranking scores.

Ranking the available reminder devices in this way allows selection of the device which will provide the highest impact on the user, when there are a plurality of reminder devices to choose from in proximity to the user.

In some embodiments, the ranking score relates to display and/or audio capabilities of the said reminder device.

Ranking the devices according to display and/or audio capabilities offers the advantage that the most suitable device can be selected depending on an individual user's requirements. For example, a user with a visual impairment may prefer to receive audio alerts.

In some embodiments, said reminder device includes a display, and the display capabilities include: a viewing angle of the display; and/or a size of the display; and/or a resolution of the display.

In some embodiments, the ranking score relates to a current activity level of the said reminder device.

In some embodiments, the system further comprises an acknowledgement receipt mechanism arranged to receive user acknowledgment of a reminder alert, wherein in response to a user acknowledgement being received, the output mechanism is arranged to stop outputting the reminder alert through the identified reminder device.

In some embodiments, in response to no user acknowledgment being received within a predetermined time after outputting the reminder alert through the selected reminder device, the reminder processor is arranged to select a different one of the plurality of reminder devices in proximity to said location of the user, and the output mechanism is arranged to output a reminder alert through the selected different reminder device.

In some embodiments, the reminder processor and output mechanism are arranged to repeatedly output reminder alerts through different ones of said plurality of reminder devices in proximity to said location of the user, until user acknowledgment is received or until no further reminder devices remain to be selected.

In some embodiments, the reminder processor is arranged to select the different reminder device by selecting one of the reminder devices with different display and/or audio capabilities to the previously selected reminder device, or is arranged to select the different reminder device by selecting the next highest ranked reminder device based on the ranking scores.

In some embodiments the system further comprises: a device information datastore arranged to store information relating to a time taken for user acknowledgment to be received in response to a reminder alert output through a said reminder device, wherein the ranking score assigned to each reminder device relates to the effectiveness of reminder alerts output through said reminder device, a reminder alert being more effective the less time is taken for user acknowledgement of the reminder alert to be received.

By recording information about the effectiveness of each reminder device on the individual user, over time the system can learn to select the most effective reminder device for providing an alert to that user. For example, audible reminders may be more effective than visual reminders for a user with a visual impairment, and so reminder alerts provided through devices with audio capabilities may be more effective.

In some embodiments, said location of the user is an expected location obtained by monitoring a location of the user over time, predicting a route that will be taken by the user, and obtaining the expected location of the user at the time at which the reminder is due from the predicted route.

In some embodiments, the locating mechanism is arranged to receive the information about the location of the user from a location sensor carried by the user.

Receiving the user's location from a sensor carried by the user, for example a Global Positioning System (GPS) receiver, allows the current location of the user to be determined with high accuracy.

In some embodiments, the system is arranged to adjust a volume level and/or a brightness level of the reminder alert according to ambient sound and/or light levels at the identified reminder device.

In some embodiments, the system further comprises: a medication dispenser arranged to communicate with the reminder processor, the medication dispenser being arranged to issue a reminder alert, at the time at which the reminder is due, unless a reminder cancel signal is received from the reminder processor, wherein the reminder processor is arranged to send the reminder cancel signal to the medication dispenser in response to said location of the user not being in proximity to a known location of the medication dispenser.

According to another aspect of the present invention, there is provided a method of providing a reminder to a user, the method comprising: accessing reminder information relating to a task for the user to be reminded about; determining a time at which the reminder is due, based on the reminder information; obtaining information relating to a location of the user for the time at which the reminder is due; identifying a reminder device in proximity to said location of the user, based on known locations of one or more reminder devices, and outputting a reminder alert through the identified reminder device.

A computer-readable storage medium can be arranged to store a computer program which, when executed, performs the method.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
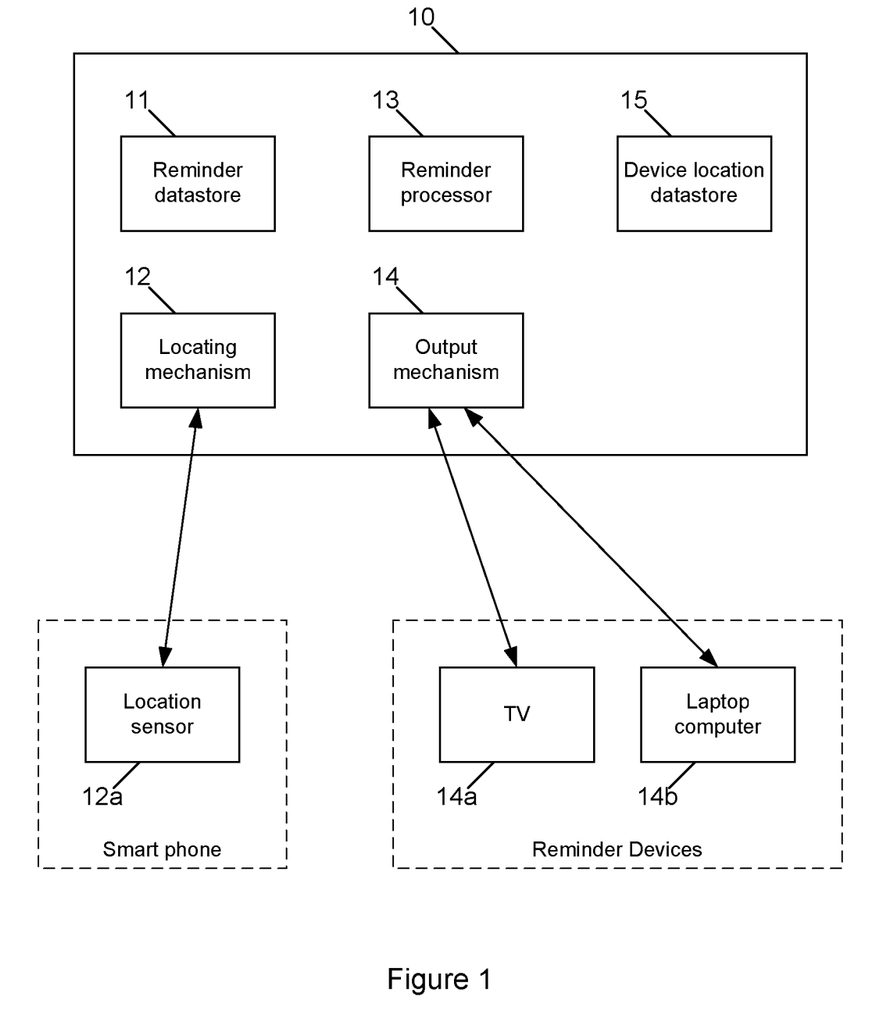
FIG. 1 schematically shows a system for reminding a user according to a first embodiment of the invention.

FIG. 1 schematically shows a system 10 for reminding a user according to a first embodiment of the invention.

The system 10 comprises a reminder datastore 11, a locating mechanism 12, a reminder processor 13, an output mechanism 14, and a device information datastore 15.

The reminder datastore 11 is arranged to store reminder information about reminders relevant to the user. In the present embodiment, the reminder datastore 11 is arranged to store information relating to a task for the user to be reminded about a certain task in relation to a therapeutic regime. For example, the user may require a reminder to take a certain dose of medication at a certain time each day. However, the invention is not limited to reminders relating to a therapeutic regime. In embodiments of the invention, the reminders can relate to any task for the user to be reminded about.

The locating mechanism 12 is arranged to obtain location information relating to a location of the user. The location information can, for example, be specific location coordinates, or can be a defined area within which the user is currently located. In this embodiment, the locating mechanism 12 includes a wireless interface for receiving location coordinates from a Global Positioning System (GPS) receiver in a smart phone carried by the user.

The reminder processor 13 is arranged to determine a time at which the reminder is due, based on the reminder information. In the present embodiment, the reminder information defines a specific time at which the reminder is due.

The output mechanism 14 is arranged to output reminder alerts to the user through one or more reminder devices 14a, 14b. In many cases a reminder alert will take the form of an audible and/or visual alert, but other types of reminder alert are also possible, for example a tactile signal from a vibration motor in a mobile phone.

The reminder processor 13 is further arranged to obtain information relating to a location of the user for the time at which the reminder is due, from the locating mechanism 12, and to identify one of the reminder devices 14a, 14b in proximity to said location of the user, based on known locations of the reminder devices 14a, 14b. Then, the output mechanism 14 is arranged to output a reminder alert through the identified reminder device.

In this embodiment, the system 10 includes a device location datastore 15 arranged to store information identifying the location of each of the reminder devices 14a, 14b, and the reminder processor 13 is arranged to obtain the known locations of the reminder devices 14a, 14b from the device location datastore 15.

The reminder devices 14a, 14b do not have to be dedicated devices, but can be any devices capable of providing a reminder to a user. In this embodiment, the reminder devices include a television (TV) 14a, and a laptop computer 14b. In embodiments of the invention, any number of reminder devices may be provided. Other examples of suitable reminder devices include electronic advertising hoardings, radios, smart phones, intelligent lighting systems, and so on. For example, a visual reminder could be output through a connected light fitting, such as a light emitting diode (LED) bulb controllable by a smart phone or other device. In the present embodiment, the output mechanism 14 communicates with the reminder devices 14a, 14b through a web-based interface, and can therefore access any suitable reminder device that includes an Internet connection. In other embodiments, the output mechanism may communicate with various ones of the reminder devices over different types of interface.

In this embodiment, the reminder datastore 11, the locating mechanism 12, the reminder processor 13, the output mechanism 14, and the device location datastore 15 are provided on the same apparatus, i.e. the same device 10. For example, such an apparatus could be a smart phone, tablet, general purpose computer, Internet server, or other suitable apparatus. In other embodiments, the elements of the system could be provided on different devices. The various components of the system 10 can be embodied as hardware or as software instructions executed by a processor.

In this embodiment, the reminder datastore 11 and the device location datastore 15 are arranged to access the reminder information and device location information from a local storage unit included in the same device 10. However, it is not necessary for the data accessed by the reminder datastore 11 and the device location datastore 15 to be physically stored within the system 10. In other embodiments the reminder information and/or the device location information can be accessed from a remote storage unit by the reminder datastore 11 and/or the device location datastore 15. For example, the reminder datastore 11 may access reminder information stored on an Internet server.

Figure 2:
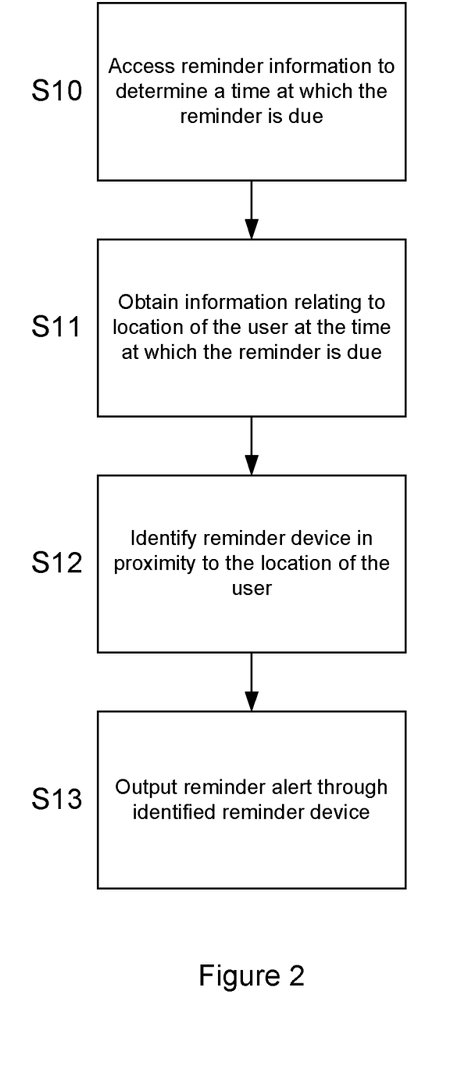
FIG. 2 shows a flow diagram explaining the operation of the system of the first embodiment.

FIG. 2 shows a flow diagram explaining the operation of the system 10 of FIG. 1.

At step S10 of FIG. 2, the system 10 accesses reminder information in order to determine a time at which the reminder is due. As described above, in the present embodiment the reminder information specifies the time at which the reminder is due. However, the invention is not limited to this approach. In another embodiment, the reminder processor 13 of the system 10 can select a different time close to the time specified by the reminder information. For example, the user could define preferred time slots in which they would like to receive reminders, and the reminder processor 13 can select the closest time within a user-preferred time slot to the time defined by the reminder information. As a further alternative, the reminder information may define a time window in which the reminder can be provided, and the reminder processor 13 can select a convenient time to provide the reminder within this time window, for example by waiting until the user approaches within a certain minimum range of one of the reminder devices 14a, 14b.

In some embodiments that use a predetermined time window for the reminders, the system 10 will ensure that the reminder is always output by the end of the predetermined time window. This could be done by outputting the reminder at the very end of the predetermined time window, regardless of the current location of the user. For example, at the end of the time window the reminder could be output through the closest reminder device to the user, regardless of the distance between that reminder device and the user's current location. In this scenario, the user may still be able to receive the reminder, for example another person nearby the reminder device could notice the reminder and contact the user to pass on the information.

The reminder information could be obtained in a variety of different ways. For example, the user can set an alarm for a certain time on a certain day. In the case of reminder information relating to a therapeutic regime, the reminder information could be obtained by a health care professional uploading a care plan that includes data such as medication, exercise regime, and diet plan that the patient needs to adhere to. The reminder information could contain reminders for tasks associated with all aspects of this care plan. In other embodiments, a health care professional could scan a bar code relating to a medication (or enter a suitable reference number), which would load information on the medication including the schedule for taking it. In other embodiments, the details could be obtained by the reminder datastore 11 in other ways, for example by manual input.

At step S11 of FIG. 2, the system 10 obtains information relating to the location of the user for the time at which the reminder is due. In this embodiment, the locating mechanism 12 of the system 10 obtains the current location of the user a short time before the time at which the reminder is due. The reminder processor 12 is arranged to assume that this will be the location of the user at the time at which the reminder is due.

In some embodiments however, instead of using the current location of the user, the system 10 may obtain an expected location of the user. For example, the location of the user could be monitored over time, in order to predict a route that will be taken by the user. The expected location of the user, which is the user's location at the time at which the reminder is due, can then be obtained from the predicted route. Here, the functions of monitoring the user's location, predicting a route, and obtaining the expected location, could be performed by any of the location sensor 12a, locating mechanism 12, or reminder processor 13. For example, the reminder processor 13 of the system 10 could regularly receive location updates from the locating mechanism 12, and perform all the processing necessary to obtain the expected location. Another approach would be for the processing to be performed locally at the location sensor 12a, for example by an application (app) running on the user's smart phone, and the expected location could then be transmitted to the reminder processor 13 via the locating mechanism 12.

It will be understood that in some situations the expected location may be predicted with greater accuracy than in other situations. For example, the expected location may be predicted with high accuracy when the user is travelling at constant speed on a well-defined route, such as a motorway or railway line. In scenarios where the user has more freedom of movement, for example when walking around a shopping Centre, the expected location may be predicted with lower accuracy.

In the present embodiment the locating mechanism 12 of the system 10 is arranged to receive the location information wirelessly from a location sensor 12a carried by the user, in the form of location coordinates. For example, the location sensor 12a can be a Global Navigation Satellite System (GNSS) receiver, such as a Global Positioning System (GPS) receiver, included in a smart phone or other device carried by the user.

In other embodiments, instead of receiving information relating to the user's location from a location sensor, the locating mechanism 12 can obtain the location information from a different source. For example, smart phone applications are known which periodically determine the device's location, e.g. using GPS, the known coordinates of a nearby telecommunications mast, triangulation techniques based on at least three base-stations or wireless access points, inertial tracking of the relative movement of a smart phone from the last known absolute location, or a combination of these techniques, and upload this information to a server. Therefore in certain embodiments of the invention, the locating mechanism 12 could query a server to retrieve the most recently updated location of the user.

At step S12 of FIG. 2, the system 10 identifies a reminder device in proximity to the location of the user obtained in step S11. As described above, the reminder processor 13 of the system 10 identifies the reminder device based on known locations of one or more reminder devices. In this embodiment, the locations of the reminder devices are determined from device location information accessed through the device location datastore 15 of the system.

The device location datastore 15 can, for example, obtain the device location information from an Internet database of available reminder devices. The device location datastore 15 could periodically retrieve updated device location information for any nearby devices from the database, or could only request relevant information at (or close to) a time when a reminder is due. In the latter case, the device location datastore 15 may be arranged to only retrieve device location information relating to reminder devices within a specific area, which can be defined based on the location of the user. For example, the device location datastore 15 may request device location information for any reminder devices within a certain radius, e.g. 5 meters, of the user's location. Retrieving the device location information from an Internet server has the advantage that the information can be centrally stored and updated.

In another embodiment, the system 10 can generate the device location information itself by performing a reminder device discovery process, to detect local accessible devices directly. This approach allows device location information to be dynamically generated as and when it is required, without having to maintain a more permanent device information datastore. In such embodiments, the device location information may only be stored in a temporary device information datastore, for example in volatile random access memory (RAM). The device discovery process may use, for example, the IEEE 802.11 device discovery process. In some embodiments, device discovery may be implemented using close proximity communication mechanisms, such as Bluetooth. For example, a device which includes the location sensor 12a, such as a smart-phone, may also include a Bluetooth communication unit which can be used to discover local reminder devices in the vicinity. Device discovery protocols may also be implemented using infra-red or other forms of localized coded light communication. In some embodiments, the discovery process can include an analytical element, wherein an emission (acoustic, visual etc.) of the device to be discovered is detected and used to trigger its further discovery. That is, the system can detect an emitted signal (e.g. acoustic, visual) characteristic of a known type of reminder device, and in response to the characteristic signal being detected, can initiate a discovery process to discover specific information about the reminder device, for example a device identifier.

Once the reminder device has been identified at step S12, then at step S13, the output mechanism 14 of the system 10 outputs a reminder alert through the identified one of the reminder devices 14a, 14b. The reminder alert could simply be a basic audio or visual signal without conveying detailed information to the user, for example a flashing display or an alarm noise. Alternatively, the output mechanism 14 can output a more detailed reminder alert through the reminder device, by transmitting more detailed information to the reminder device. For example, the output mechanism 14 may transmit a message to be displayed or reproduced audibly as the reminder alert, the message including information about the task to which the reminder relates.

Figure 3:
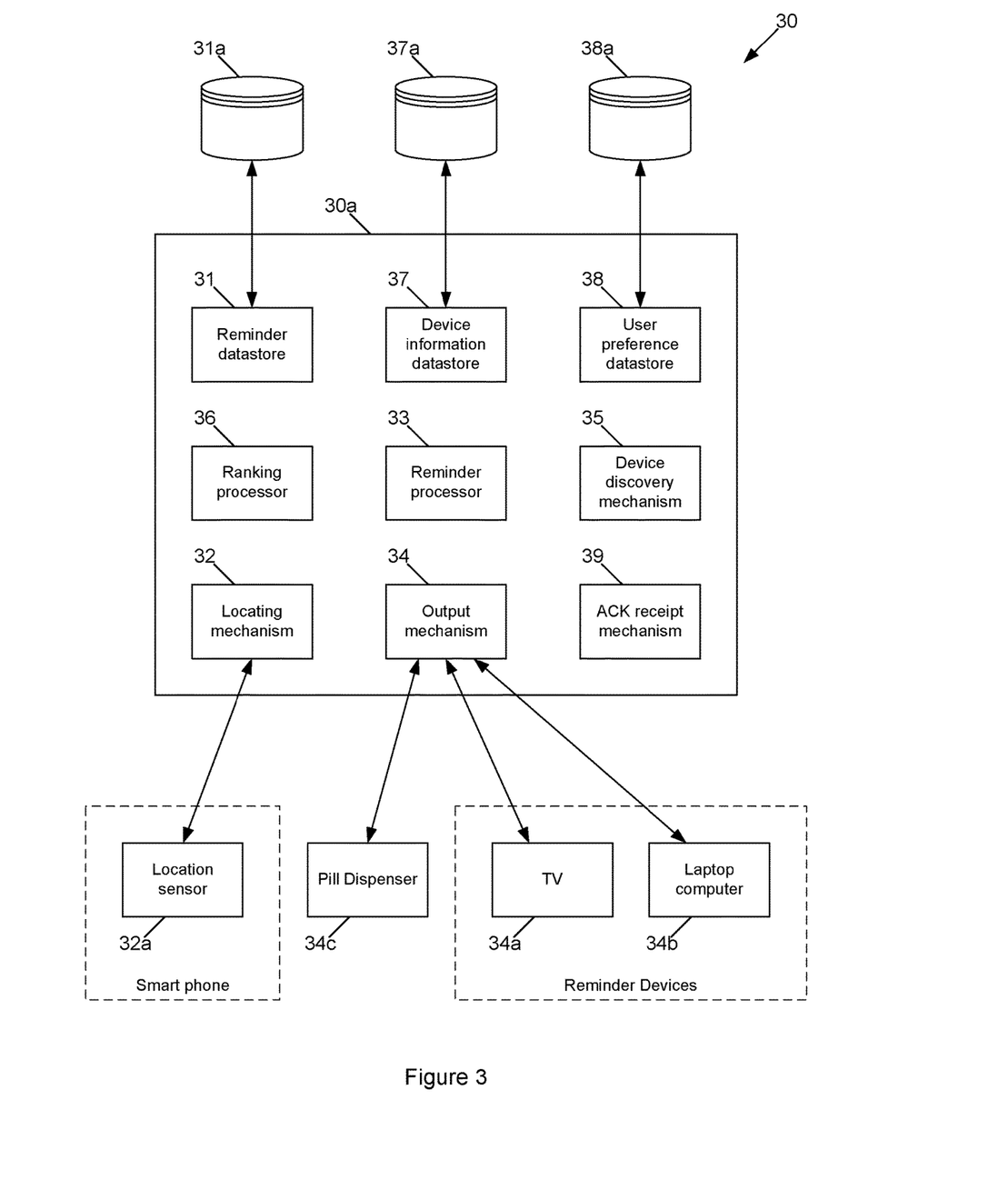
FIG. 3 schematically shows a system for reminding a user according to a second embodiment of the invention.

FIG. 3 schematically shows a system 30 for reminding a user according to a second embodiment of the invention. In this embodiment, the system 30 is specifically arranged to monitor the user's adherence to a medication regime. As a result, the user in the context of this embodiment is a patent with a long term health condition that requires a therapeutic regime into order to keep the user's long term health condition stable. In this example embodiment, it will be assumed that non-adherence with the user's therapeutic regime will lead to a worsening of the patient's symptoms. The system 30 is arranged to provide reminders to promote adherence to the therapeutic regime.

The system 30 comprises a device 30a and a number of remote devices, including a remote reminder database 31a, a remote device information database 37a, a remote user preference database 38a, a remote location sensor 32a, a number of reminder devices 34a, 34b, and a remote pill dispenser 34c.

The device 30a comprises a reminder datastore 31, a locating mechanism 32, a reminder processor 33, and an output mechanism 34, which are similar to the corresponding components in the system 10 of FIG. 1. A detailed description of these similar components will be omitted here, to preserve brevity. In addition, the device 30a comprises a device discovery mechanism 35, a ranking processor 36, a device information datastore 37, a user preference datastore 38, and an acknowledgement receipt mechanism 39.

The acknowledgement receipt mechanism 39 is arranged to receive user acknowledgement of a reminder alert. The user acknowledgement can be received through any suitable user interface. For example, the user acknowledgement can be received through a user interface included in the device 30a, or through another device such as a smart phone. In another embodiment, the user acknowledgement could be received directly from one of the reminder devices 34a, 34b or the pill dispenser 34c.

The device 30a is in communication with the remote reminder database 31a, the remote device information database 37a, the remote user preference database 38a, the remote location sensor 32a, the reminder devices 34a, 34b, and the remote pill dispenser 3 via suitable interfaces. For example, the device 30a could be connected to the remote reminder database 31 a, the remote device information database 37a and the remote user preference database 38a via a network, such as the Internet. Depending on the distances involved, the device 30a could also be connected to the other remote devices including the remote location sensor 32a, the reminder devices 34a, 34b, and the remote pill dispenser 3 via a network such as the Internet, or via a short range wireless connection, such as Bluetooth. It will, however, be appreciated that other embodiments could use other ways of connecting the remote devices to the device 30a.

In this embodiment, the device 30a is a portable device (e.g. a smart phone) carried by the user. In other embodiments, the device 30a could be a standalone device that is not portable. In other embodiments, the device 30a could be integrated into the functionality of a general purpose device, or could be an Internet server.

In this embodiment, the pill dispenser 34c can provide audible and/or visual reminder alerts. The output mechanism 34 is capable of instructing the pill dispenser 34c whether or not to provide an audible and visual alert, and can also interface with the TV 34a or laptop computer 34b to output audible and/or visual reminder alerts.

Figure 4:
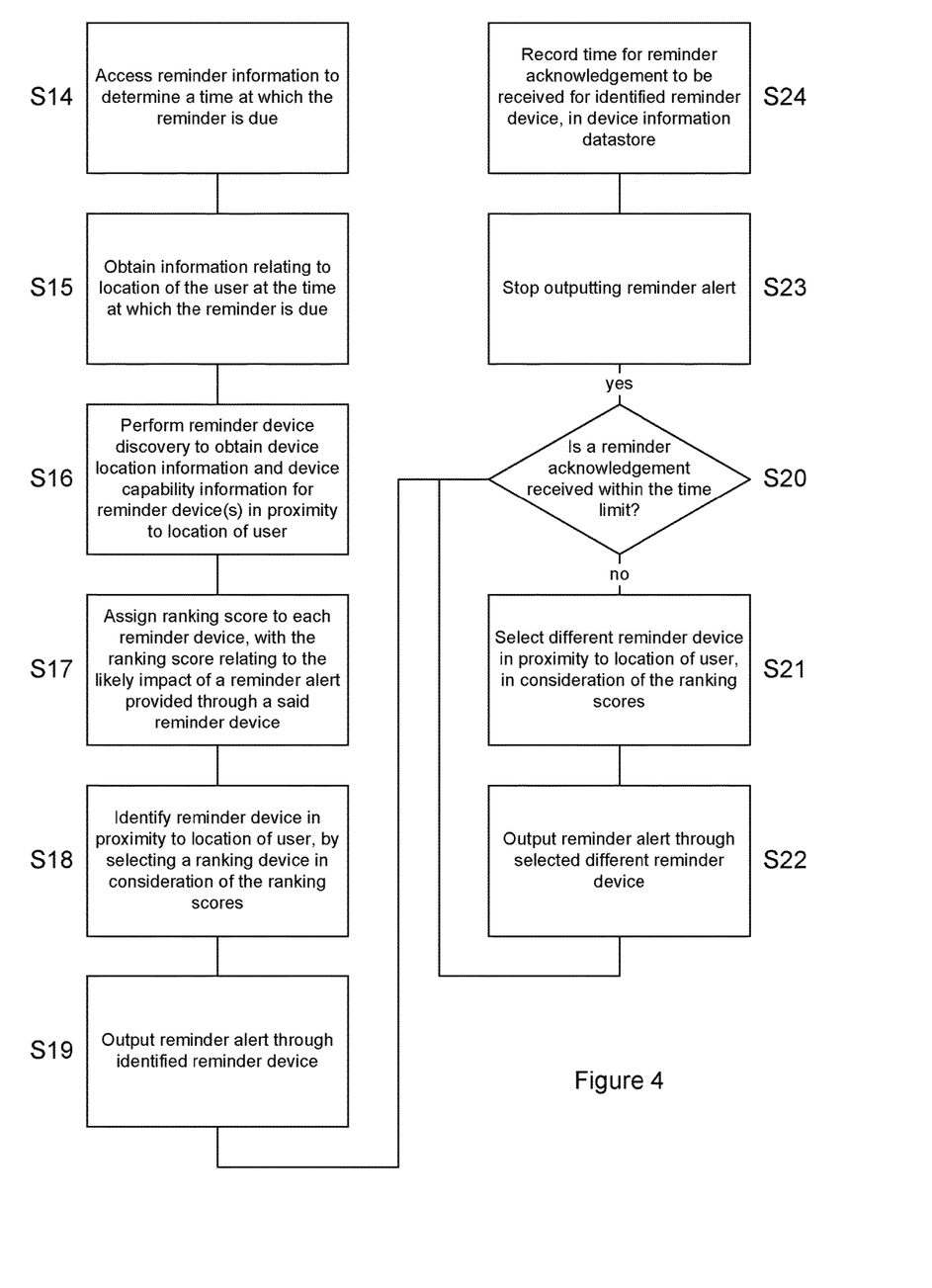
FIG. 4 shows a flow diagram explaining the operation of the system of the second embodiment.

FIG. 4 shows a flow diagram explaining the operation of the system 30 of FIG. 3.

Steps S14 and S15 of FIG. 4 are similar to steps S10 and S11 of FIG. 2, and a detailed description will not be repeated here.

At step S16 of FIG. 4, after obtaining the location of the user at the time at which the reminder is due, the device discovery mechanism 35 of the system 30 performs device discovery. During the device discovery process, the device discovery mechanism 35 obtains the device location information for any reminder devices in proximity to the obtained location of the user. Also, the device discovery mechanism 35 obtains device capability information for each reminder device. The device capability information can, for example, include information about audio and/or video capabilities of each reminder device.

For example, the device discovery mechanism 35 can broadcast a request for any available reminder devices in a specified area to reply with their location and capability information. In this embodiment, the device location datastore 15 of FIG. 1 is not required since the device location information is obtained dynamically, as and when it is required.

The device discovery process may use, for example, the IEEE 802.11 device discovery process. Further details may be found in chapter I.A. "The IEEE 802.11 Discovery Process" in the paper "A study of the discovery process in 802.11 networks", authored by German Castignani et al., and other sources including relevant IEE standards documents. It will be appreciated that different protocols and technologies will be suitable for different proximities from the reminder devices and different modes of operating.

Although device discovery is used in the present embodiment to obtain the device location information and device capability information, in other embodiments step S16 can be omitted. For example, instead of performing device discovery, the device location information and device capability information could be retrieved from the device information datastore 37 or another suitable datastore, and the device discovery mechanism 35 could be omitted.

Furthermore, in some embodiments a combination of these approaches could be used. For example, the device location information could be obtained through device discovery, and the device capability information could be retrieved from a datastore. Device capabilities are likely to remain fixed, and so it may not be necessary for new capability information to be obtained each time during device discovery.

At step S17 of FIG. 4, the ranking processor 36 of the system 30 assigns a ranking score to each of the reminder devices. The ranking score for a reminder device relates to the likely impact of a reminder alert provided through that reminder device. The ranking scores enable the reminder devices to be ranked according to the likely impact of a reminder alert, and hereinafter a reminder device with a higher likely impact will be described as having a higher ranking This does not mean that the ranking score for such a device has a higher numerical value, since a ranking system could be used in which a lower numerical value is associated with a higher impact. In this case the reminder device with the lowest numerical score would be considered the "highest-ranked" device, that is, the device with the highest impact.

In this embodiment, the ranking processor 36 also takes into account user preferences stored in the user preference datastore 38. For example, a user may prefer to receive audio alerts rather than visual alerts, and so the ranking processor 36 may assign a higher ranking score to a reminder device with audio capabilities than to a reminder device without audio capabilities.

Ranking the available reminder devices in this way allows selection of the device which will provide the highest impact on the user, when there are a plurality of reminder devices to choose from in proximity to the user.

In some embodiments, the ranking score relates to display and/or audio capabilities of the said reminder device. Examples of display capabilities that can be taken into account when assigning ranking scores include, but are not limited to: a viewing angle of the display; and/or a size of the display; and/or a resolution of the display. Ranking the devices according to display and/or audio capabilities offers the advantage that the most suitable device can be selected depending on an individual user's requirements. For example, a user with a visual impairment may prefer to receive audio alerts.

Also, in some embodiments, the ranking score relates to a current activity level of the said reminder device. This can avoid the system attempting to output a reminder alert through a device which is already in use for a task which should not be interrupted. In other words, if the said reminder device is active (e.g. being used by the user), then the ranking score for that device could be lowered. For example, if the reminder device is a smartphone, the ranking score for the smartphone could be lower if the smartphone is being used by the user to make a call.

Such embodiments may categorize different activities of the reminder devices in different ways. For example, again considering the reminder device being a smartphone, the system may be arranged such that if the user is using the smartphone for the activity of reading text messages, this current activity level of the smartphone may be considered not to impact on the effectiveness of a reminder sent via the smartphone, for example because the user may be happy to be interrupted while reading text messages, and hence the hence the ranking of the smartphone may be unadjusted. However, for the activity of receiving a phone call, this current activity level of the smartphone may be considered to impact on the effectiveness of a reminder sent via the smartphone, and hence the ranking of the smartphone may be lowered.

In some embodiments, the ranking score relates to a user preference regarding their preferred reminder device or preferred type of reminder device (e.g. visual or audible).

At step S18 of FIG. 4, the reminder processor 33 of the system 30 is arranged to identify the reminder device by selecting one of a plurality of the reminder devices in proximity to said location of the user, in consideration of the ranking scores. For example, the reminder processor 33 can simply select the device with the highest ranking If necessary, the reminder processor 33 could also take into account factors not considered by the ranking processor 36 when assigning ranking scores. For example, in some embodiments the ranking scores could be assigned before up-to-date information about the user's location is available. In this case, the ranking processor 36 cannot take into account distance from the user when assigning ranking scores. Therefore when two reminder devices have similar ranking scores, the ranking processor 33 may preferentially choose the reminder device closest to the user.

In some embodiments, ranking may not be performed, and steps S17 and S18 can be omitted.

At step S19 of FIG. 4, the output mechanism 34 outputs a reminder alert through the reminder device identified in step S18, in a similar manner to step S13 of FIG. 1.

At step S20 of FIG. 4, the system 30 waits for a user acknowledgement of the reminder alert to be received through the acknowledgement receipt mechanism 39 of the system 30. In the present embodiment the system 30 waits for a predetermined time limit, but in other embodiments the system 30 could wait indefinitely and take no further action if an acknowledgement is never received.

At step S21 of FIG. 4, in response to no user acknowledgment being received within the time limit after outputting the reminder alert through the selected reminder device, the reminder processor 33 of the system 30 is arranged to select a different one of the plurality of reminder devices in proximity to the user's location.

In this embodiment, the reminder processor 33 is arranged to select the different reminder device by selecting the next highest ranked reminder device based on the ranking scores. In another embodiment, the reminder processor 33 can be arranged to select the different reminder device by selecting one of the reminder devices with different display and/or audio capabilities to the previously-selected reminder device.

At step S22 of FIG. 4, the output mechanism 34 of the system 30 is arranged to output a reminder alert through the selected different reminder device. Here, the output mechanism 34 can also continue to output the previous reminder alert through the previously-selected reminder device, or can cancel the previous reminder alert. The system 30 then returns to step S20 and waits for acknowledgement of the new reminder alert.

This time, at step S20 the system 30 can wait for the same time period as before, or can wait for a different time period. For example, in some embodiments the system can wait for a shorter time period each time a different device is selected, since when several reminders have been ignored this may be an indication that the user is unable to acknowledge the reminders, for instance the user may be asleep or busy.

The system may be arranged to repeat steps S20 through S22 until a user acknowledgment is received, until a predetermined number of reminders have been issued, or until no further reminder devices remain to be selected. In some embodiments, steps S21 and S22 may be omitted altogether, in which case the system will only output a single reminder.

Once a user acknowledgement is received in step S20, then the system proceeds to step S23. At step S23 of FIG. 4, the output mechanism 34 of system 30 is arranged to stop outputting the reminder alert through the currently-selected reminder device, and through any other reminder devices that are still outputting earlier reminder alerts for the same task.

In some embodiments, the acknowledgement receipt mechanism 39 can be omitted, as in FIG. 1. In such embodiments, the system may be arranged to cancel the reminder alert after a predetermined time period.

At step S24 of FIG. 4, the system 30 updates the device information datastore 37 based on a time taken for the user acknowledgment to be received. The device information datastore 37 is arranged to store information relating to a time taken for user acknowledgment to be received in response to a reminder alert output through a reminder device. This information can be taken into account by the ranking processor 36 when assigning ranking scores. Specifically, the ranking score assigned to each reminder device can relate to the effectiveness of reminder alerts output through said reminder device, a reminder alert being more effective the less time is taken for user acknowledgement of the reminder alert to be received.

By recording information about the effectiveness of each reminder device on the individual user, over time the system can learn to select the most effective reminder device for providing an alert to that user. For example, audible reminders may be more effective than visual reminders for a user with a visual impairment, and so reminder alerts provided through devices with audio capabilities may be more effective.

Figure 5:
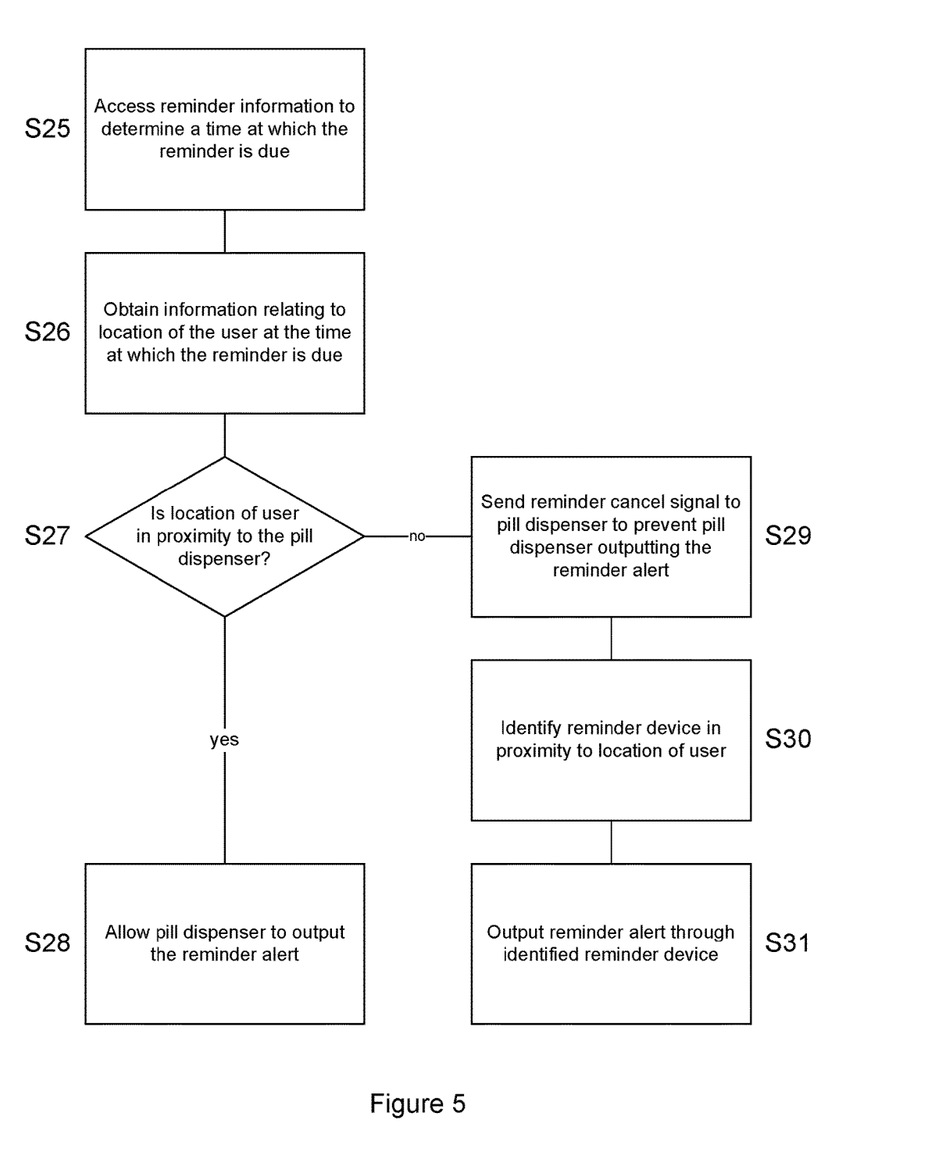
FIG. 5 shows a flow diagram explaining a method of controlling a reminder alert output by a pill dispenser in the system of the second embodiment.

FIG. 5 shows a flow diagram explaining a method of controlling a reminder alert output by the pill dispenser 34c in the system 30 of the second embodiment. The pill dispenser 34c is arranged to communicate with the reminder processor 33, and is arranged to issue a reminder alert, at the time at which the reminder is due, unless a reminder cancel signal is received from the reminder processor. That is, the pill dispenser 34c also has access to the reminder information, for example through the reminder datastore 31 or through a duplicate copy of the reminder information stored locally in a memory included in the pill dispenser 34c.

Steps S25 and S26 of FIG. 5 are similar to steps S10 and S11 of FIG. 2, and a detailed description will not be repeated here.

At step S27 of FIG. 5, the reminder processor 33 of system 30 checks whether the user's current location is in proximity to the pill dispenser 34c, for example by checking whether the user's location is within a predetermined range of the pill dispenser 34c. In response to a determination that the user is currently in proximity to the pill dispenser 34c, then in step S28 the system 30 takes no further action, and allows the pill dispenser 34c to output the reminder alert.

On the other hand, in response to a determination that the user is not in proximity to the pill dispenser in step S27, then the system 30 proceeds to step S29. In step S29 of FIG. 5, the reminder processor 33 is arranged to send the reminder cancel signal to the pill dispenser 34c in response to said location of the user not being in proximity to a known location of the pill dispenser 34c.

The system 30 then proceeds through steps S30 and S31 to output a reminder alert through a reminder device in proximity to the user. Steps S30 and S31 are similar to steps S12 and S13 of FIG. 2, and a detailed description will not be repeated here.

In this embodiment, the pill dispenser 34c automatically issues its own reminder alert unless signaled otherwise by the device 30a. However, in another embodiment the pill dispenser 34c can behave as any other reminder device, that is, the pill dispenser 34c could only issue a reminder alert when controlled to do so by the output mechanism 34.

Although a pill dispenser is described in the present embodiment, in embodiments of the present invention any type of medication dispenser could be used, whether the medication is in the form of pills or otherwise.

Figure 6:
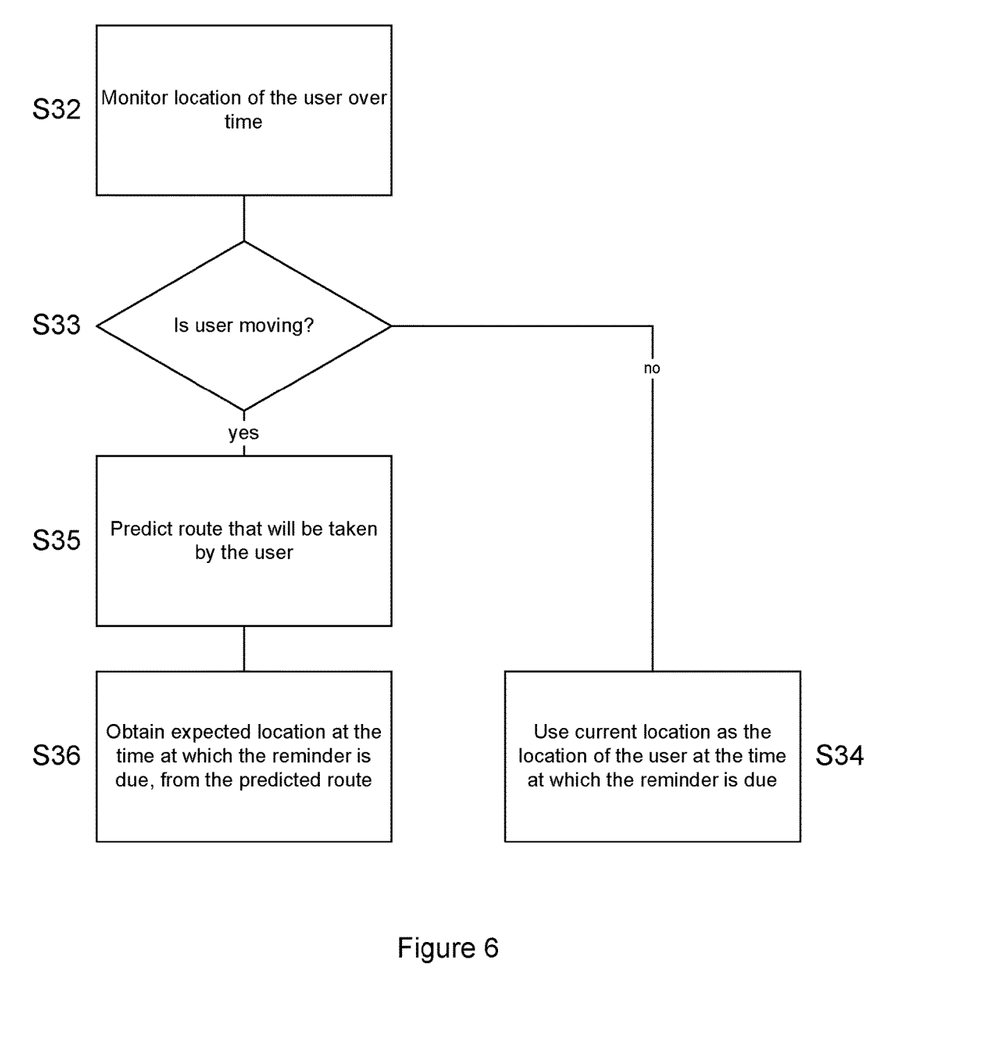
FIG. 6 shows a flow diagram explaining a method of obtaining information about the location of the user, for use by the systems of the first or second embodiments.

FIG. 6 shows a flow diagram explaining a method of obtaining information about the location of the user, for use by the systems of the first or second embodiments. That is, the steps shown in FIG. 6 can be performed during step S11 of FIG. 2 or step S15 of FIG. 4.

At step S32 of FIG. 6, the system monitors the location of the user over time, and at step S33, it is checked whether the user is moving. In response to a determination that the user is not moving, then in step S34 the user's current location is taken as being the user location at the time when the reminder is due, since the user is currently stationary. In some embodiments, the current location may be used whenever it is determined that the user is only moving slowly, i.e. slower than a threshold speed.

In response to a determination that the user is currently moving, then in step S35 a route that will be taken by the user is predicted, and in step S36 the expected location of the user at the time at which the reminder is due is obtained from the predicted route.

It will be appreciated that the hardware used by embodiments of the invention can take a number of different forms. For example, all the components of the system could be provided by a single device (e.g. the example of FIG. 1), or different components of the system could be provided on separate devices. An examples of such an arrangement is the system of FIG. 3, in which a number of the components of the respective systems are provided on a device, whereas other components are provided on remote devices (with "remote" in this context meaning not part of the device, but communicable with the device). More generally, it will be appreciated that embodiments of the invention can provide a system that comprises one device or several devices in communication.

In some embodiments, a volume level and/or a brightness level of the reminder alert can be adjusted according to ambient sound and/or light levels at the identified reminder device. For example, in some embodiments the system 10 can include one or more sensors arranged to detect ambient sound and/or light levels in the vicinity of the identified reminder device, and the output mechanism can control the identified reminder device to output the reminder alert at a level (e.g. volume/brightness level) appropriate to the ambient conditions. For instance, in a quiet environment a reminder alert can be issued at a relatively low volume level, whereas in a noisy environment, a reminder alert can be issued at a relatively high volume level to ensure that the reminder alert is heard by a user. In other embodiments, a reminder device can automatically adjust the volume and/or brightness level of the reminder alert by directly sensing the ambient conditions, independently of the reminder control system 10.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A system for providing a reminder to a user, the system comprising:
   a reminder datastore arranged to store reminder information relating to a task for the user to be reminded about;
   a reminder processor arranged to determine a time at which the reminder is due, based on the reminder information;
   a locating mechanism arranged to obtain information relating to a location of the user;
   an output mechanism arranged to output reminder alerts through a plurality of reminder devices; and
   a ranking processor arranged to assign a ranking score to individual reminder devices, with the ranking score relating to the likely impact of a reminder alert provided through a given reminder device,
   wherein the ranking processor is configured to obtain information indicating current activity levels of the individual reminder devices for the time at which the reminder is due, the current activity levels indication operations performed by the individual reminder devices such that the given reminder device has a first ranking score responsive to performing a first current operation and a second ranking score responsive to performing a second current operation;
   wherein the reminder processor is arranged to obtain information relating to a location of the user for the time at which the reminder is due, from the locating mechanism, and to identify a reminder device which will provide the highest impact on the user by selecting one of the plurality of reminder devices which is in proximity to said location of the user, based on known locations of the individual reminder devices and the operations performed by the individual reminder devices at the time for the reminder, in consideration of the ranking scores, and
   wherein the output mechanism is arranged to output a reminder alert through the identified reminder device.

2. The system of claim 1, wherein the ranking scores further relate to display and/or audio capabilities of individual reminder devices.

3. The system of claim 2, wherein the ranking scores relate to the display capabilities of individual reminder devices, wherein the given reminder device includes a display, and the display capabilities include:
   a viewing angle of the display; and/or a size of the display; and/or
   a resolution of the display.

4. The system of claim 1, wherein the ranking scores relate to a user preference regarding their preferred reminder device or preferred type of reminder device.

5. The system of claim 1, further comprising:
an acknowledgement receipt mechanism arranged to receive user acknowledgment of a reminder alert,
wherein in response to a user acknowledgement being received, the output mechanism is arranged to stop outputting the reminder alert through the identified reminder device.

6. The system of claim 5, wherein in response to no user acknowledgment being received within a predetermined time after outputting the reminder alert through the selected reminder device, the reminder processor is arranged to select a different one of the plurality of reminder devices in proximity to said location of the user, and the output mechanism is arranged to output a reminder alert through the selected different reminder device.

7. The system of claim 6, wherein the reminder processor and output mechanism are arranged to repeatedly output reminder alerts through different ones of the plurality of reminder devices in proximity to said location of the user, until user acknowledgment is received or until no further reminder devices remain to be selected.

8. The system of claim 6, wherein the reminder processor is arranged to select the different reminder devices by selecting one of the reminder devices with different display and/or audio capabilities relative to a previously selected reminder device, or
wherein the reminder processor is arranged to select the different reminder devices by selecting a next highest ranked reminder device based on ranking scores.

9. The system of claim 5, further comprising:
a device information datastore arranged to store information relating to a time taken for user acknowledgment to be received in response to a reminder alert output through the identified reminder device,
wherein the ranking score assigned to each reminder device relates to the effectiveness of reminder alerts output through said reminder devices, a reminder alert being more effective the less time is taken for user acknowledgement of the reminder alert to be received.

10. The system of claim 1, wherein said location of the user is an expected location obtained by monitoring a location of the user over time, predicting a route that will be taken by the user, and obtaining the expected location of the user at the time at which the reminder is due from the predicted route.

11. The system of claim 1, wherein the locating mechanism is arranged to receive the information about the location of the user from a location sensor carried by the user.

12. The system of claim 1, further comprising:
a medication dispenser arranged to communicate with the reminder processor, the medication dispenser being arranged to issue a reminder alert, at the time at which the reminder is due, unless a reminder cancel signal is received from the reminder processor,
wherein the reminder processor is arranged to send the reminder cancel signal to the medication dispenser in response to said location of the user not being in proximity to a known location of the medication dispenser.

13. A method of providing a reminder to a user, the method comprising:
accessing reminder information relating to a task for the user to be reminded about;
determining a time at which the reminder is due, based on the reminder information;
obtaining information relating to a location of the user for the time at which the reminder is due;
assigning a ranking score to each of a plurality of reminder devices, the ranking score relating to the likely impact of a reminder alert provided through a reminder device, wherein the ranking score indicates current activity levels of individual reminder devices for the time at which the reminder is due, the current activity levels indicating operations performed by the individual reminder devices such that a given reminder device has a first ranking score responsive to performing a first current operation and a second ranking score responsive to performing a second current operation;
identifying a reminder device which will provide the highest impact on the user by selecting one of the plurality of the reminder devices in proximity to said location of the user, based on known locations of the reminder devices and the operations performed by the individual reminder devices at the time for the reminder, in consideration of the ranking scores, and
outputting a reminder alert through the identified reminder device.

14. A physical non-transitory electronic computer-readable storage medium arranged to store a computer program which, when executed by a processor, performs the method of claim 13.

* * * * *